(12) United States Patent
Holmes-Farley et al.

(10) Patent No.: US 6,517,825 B1
(45) Date of Patent: *Feb. 11, 2003

(54) POLYETHER-BASED BILE ACID SEQUESTRANTS

(75) Inventors: Stephen Randall Holmes-Farley, Arlington, MA (US); Chad Cori Huval, Somerville, MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/713,784

(22) Filed: Nov. 15, 2000

Related U.S. Application Data

(63) Continuation of application No. 09/298,350, filed on Apr. 23, 1999, now Pat. No. 6,190,649.

(51) Int. Cl.$^7$ ................................ A61K 31/74
(52) U.S. Cl. .................. 424/78.08; 424/400; 424/484; 424/486; 424/487
(58) Field of Search ................. 424/484, 486, 424/487, 78.08

(56) References Cited

U.S. PATENT DOCUMENTS

| | | | |
|---|---|---|---|
| 3,320,317 A | 5/1967 | Rogers et al. | 260/567.6 |
| 3,850,857 A | 11/1974 | Dreyfuss | 260/2 A |
| 3,864,288 A | 2/1975 | Riew et al. | 260/2 A |
| 3,898,185 A | 8/1975 | Philp et al. | 252/511 |
| 4,056,510 A | 11/1977 | Symm et al. | 260/47 |
| 5,496,545 A | 3/1996 | Holmes-Farley et al. | 424/78.11 |
| 5,607,669 A | 3/1997 | Mandeville, III et al. | 424/78.12 |
| 5,618,530 A | 4/1997 | Mandeville, III et al. | 424/78.12 |
| 5,624,963 A | 4/1997 | Mandeville, III et al. | 514/789 |
| 5,667,775 A | 9/1997 | Holmes-Farley et al. | 424/78.11 |
| 5,679,717 A | 10/1997 | Mandeville, III et al. | 514/742 |
| 5,693,675 A | 12/1997 | Mandeville, III et al. | 514/742 |
| 5,703,188 A | 12/1997 | Mandeville, III et al. | 526/290 |
| 5,925,379 A | 7/1999 | Mandeville et al. | 424/484 |
| 5,929,184 A | 7/1999 | Holmes-Farley et al. | 526/290 |
| 6,190,649 B1 * | 2/2001 | Holmes-Farley et al. | 424/78.08 |

FOREIGN PATENT DOCUMENTS

| | | |
|---|---|---|
| DE | 2437927 A1 | 8/1974 |
| EP | 0081291 A2 | 6/1983 |
| GB | 2 036 048 A | 4/1998 |
| WO | WO 94 27620 A | 12/1994 |
| WO | WO 95 34585 A | 12/1995 |
| WO | WO 96 39449 A | 12/1996 |
| WO | WO 98/17707 | 4/1998 |

OTHER PUBLICATIONS

Patent Abstracts of Japan, vol. 1998, No. 09, Jul. 31, 1998 for JP 10 101531 A (KAO Corp.), Arp. 21, 1998.

* cited by examiner

*Primary Examiner*—Jose' G. Dees
*Assistant Examiner*—Konata M. George
(74) *Attorney, Agent, or Firm*—Hamilton, Brook, Smith & Reynolds, P.C.

(57) ABSTRACT

The present invention relates to a method for sequestering bile acids in a patient and to particular polymers for use in the method. The invention further relates to a method for reducing blood cholesterol, treating atherosclerosis, treating hypercholesterolemia and/or reducing plasma lipid content of a mammal. The methods of the invention comprise orally administering to the patient a therapeutically effective amount of a polymer characterized by a polyether backbone and amino or ammonium groups pendant therefrom. The amino nitrogen atoms can be substituted by one or more substituents independently selected from among substituted and unsubstituted, normal, branched and cyclic alkyl groups, and aryl groups. When the polymer comprises pendant ammonium or quaternary ammonium groups, the polymer will be associated with a pharmaceutically acceptable anion.

30 Claims, No Drawings

POLYETHER-BASED BILE ACID SEQUESTRANTS

RELATED APPLICATION

This application is a continuation of U.S. patent application Ser. No. 09/298,350 filed Apr. 23, 1999, now U.S. Pat. No. 6,190,649, the entire teachings of which are incorporated herein by reference.

BACKGROUND OF THE INVENTION

Biologically, cholesterol is eliminated from the body by conversion into bile acids and excretion as neutral steroids. Bile acids are synthesized from cholesterol in the liver and enter the bile as glycine and taurine conjugates. They are released in salt form in bile during digestion and act as detergents to solubilize and consequently aid in the digestion of dietary fats. Following digestion, bile acid salts are mostly reabsorbed by active transport in the ileum, complexed with proteins, and returned to the liver through hepatic portal veins. The small amount of bile acid salts not reabsorbed in the ileum is excreted via the distal ileum and large intestine, as a portion of the fecal material.

Therefore, reabsorption of bile acids, which can be present as the corresponding salts or conjugates, from the intestine conserves lipoprotein cholesterol in the bloodstream. As such, reducing reabsorption of bile acids within the intestinal tract can lower levels of bile acids circulating in the enterohepatic system thereby promoting replacement of bile acids through de novo synthesis from cholesterol, in the liver. The result is a lowering of circulating blood cholesterol levels.

One method of reducing the quantity of bile acids that are reabsorbed is the oral administration of compounds that sequester the bile acids within the intestinal tract and cannot themselves be absorbed. The sequestered bile acids consequently are excreted.

A need exists for sequestrants that bind bile acid salts and conjugates.

SUMMARY OF THE INVENTION

The present invention relates to a method for sequestering bile acids in a patient and to particular polymers for use in the method. The method comprises the step of administering to the patient a therapeutically effective amount of a polymer characterized by a polyether backbone and amino or ammonium groups pendant therefrom. The amino nitrogen atoms can be substituted by one or more substituents independently selected from among substituted and unsubstituted, normal, branched and cyclic alkyl groups, and aryl groups. When the polymer comprises pendant ammonium or quaternary ammonium groups, the polymer will be associated with a suitable anion, such as a conjugate base of a pharmaceutically acceptable acid.

The polymer to be administered can be a homopolymer or a copolymer. When the polymer is a copolymer, the polymer can comprise at least two distinct side chains.

The polymer can be linear, branched or crosslinked. In one embodiment, the polymer is crosslinked via the incorporation of a multifunctional comonomer. In another embodiment, the polymer is crosslinked via bridging groups which link amino nitrogen atoms on different polymer strands.

The invention further relates to a method for reducing blood cholesterol, treating atherosclerosis, treating hypercholesterolemia and/or reducing plasma lipid content of a mammal.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principal features of the invention can be employed in various embodiments without departing from the scope of the present invention.

In one aspect, the present invention relates to a method for sequestering bile acids in a patient and to particular polymers for use in the methods. The method comprises the step of orally administering to a mammal, such as a human, a therapeutically effective amount of a new class of polyether-based polymers comprising a polyether backbone having at least one amino or ammonium group pendant therefrom.

The invention also provides a method for reducing blood cholesterol, treating atherosclerosis, treating hypercholesterolemia and/or reducing plasma lipid content of a mammal. The methods comprises the step of orally administering to a mammal, such as a human, a therapeutically effective amount of a new class of polyether-based polymers comprising a polyether backbone having at least one amino or ammonium group pendant therefrom.

As used herein, the term "therapeutically effective amount" refers to an amount which is sufficient to bind bile acids, reduce blood cholesterol, treat atherosclerosis and/or treat hypercholesterolemia in a patient. The patient can be an animal, for example, a mammal such as a human.

In one embodiment, the polymer to be administered is characterized by a repeat unit of Formula I,

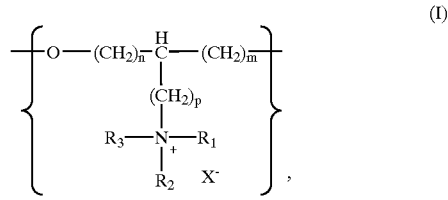

(I)

wherein n and m are each, independently, 0, 1 or 2 and p is 0 to about 6. $R_1$, $R_2$ and $R_3$ are each, independently, a hydrogen atom; a substituted or unsubstituted, linear, branched or cyclic alkyl group; or a substituted or unsubstituted aryl group. Suitable alkyl and aryl substituents include aryl groups; halogen atoms, such as fluorine, chlorine, bromine and iodine atoms; alkyl groups; hydroxy; primary, secondary and tertiary amino; quaternary ammonium; alkoxy; carboxamido; sulfonamido; aryl; hydrazido; guanidyl; and ureyl. $X^-$ is a pharmaceutically acceptable anion. Examples of suitable anions include chloride, bromide, citrate, tartrate, lactate, methanesulfonate, acetate, formate, maleate, fumarate, malate, succinate, malonate, sulfate, hydrosulfate, L-glutamate, L-aspartate, pyruvate, mucate, benzoate, glucuronate, oxalate, ascorbate, acetylglycinate, the conjugate base of a fatty acid (e.g., oleate, laurate, myristate, stearate, arachidate, behenate, arachidonate) and combinations thereof. In a preferred embodiment, $X^-$ is chloride.

In one embodiment, at least one of $R_1$, $R_2$ and $R_3$ is a hydrophobic group, preferably a hydrophobic alkyl group. "Hydrophobic group", as the term is used herein, is a chemical group which, as a separate entity, is more soluble in octanol than water. For example, the octyl group ($C_8H_{17}$) is hydrophobic because its parent alkane, octane, has greater solubility in octanol than in water. The hydrophobic group can be a saturated or unsaturated, substituted or unsubstituted hydrocarbon group. Such groups include substituted and unsubstituted, normal, branched or cyclic alkyl groups having at least about four, preferably at least about six, carbon atoms, substituted or unsubstituted arylalkyl or heteroarylalkyl groups and substituted or unsubstituted aryl or heteroaryl groups. Preferably the hydrophobic group includes an alkyl group of between about four and thirty carbon atoms. More preferably the hydrophobic group includes an alkyl group of between six and about fourteen carbon atoms. Suitable hydrophobic groups include, for example, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-eicosyl. Other examples of hydrophobic groups include haloalkyl groups of at least about four, preferably about six, carbon atoms (e.g., 10-halodecyl), hydroxyalkyl groups of at least about four, preferably about six, carbon atoms (e.g., 11-hydroxyundecyl), and aralkyl groups (e.g., benzyl).

The polymer to be administered can also be characterized by a repeat unit of Formula I in which one of the substituents $R_1$, $R_2$ and $R_3$ is absent. For example, when at least one of $R_1$, $R_2$ and $R_3$ is a hydrogen atom, the repeat unit can also exist in the deprotonated basic form.

In one embodiment, the polymer to be administered is characterized by a repeat unit of Formula I wherein n is 1, m is 0 and p is 1. In this embodiment, the polymer can be, for example, an amino- or ammonium-substituted poly (epichlorohydrin) polymer.

The polymer to be administered can be a homopolymer or a copolymer. In one embodiment, the polymer is a copolymer characterized by two different repeat units of Formula I in which at least one of $R_1$, $R_2$ and $R_3$ in the first repeat unit of Formula I differs from $R_1$, $R_2$ or $R_3$ in the second repeat unit of Formula I. In another embodiment, the polymer is a copolymer characterized by a first repeat unit of Formula I and a second repeat unit of Formula II,

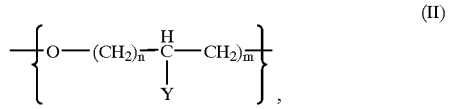

(II)

where n and m are each, independently, 0, 1 or 2 and Y is a hydrogen atom, an alkyl group or a chloromethyl group. In a preferred embodiment, n is 1 and m is 0.

In one embodiment, the polymer to be administered is characterized by a repeat unit of Formula I wherein at least one of $R_1$, $R_2$ and $R_3$ is an ammonioalkyl group.

Suitable ammonioalkyl group are of the general formula:

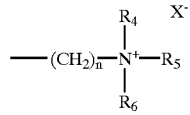

wherein $R_4$, $R_5$ and $R_6$ are each, independently, a hydrogen atom or a $C_1$–$C_{30}$ alkyl group; n is an integer from 2 to about 20, preferably from 3 to about 6; and $X^-$ is a pharmaceutically acceptable anion as discussed above. In one embodiment, at least one of $R_4$, $R_5$ and $R_6$ is a hydrophobic alkyl group having from 4 to about thirty carbon atoms. In another embodiment, the alkylene group, —$(CH_2)_n$— can be substituted with a suitable substituent as described above. Suitable examples of ammonioalkyl groups include, but are not limited to, 4-(dioctylmethylammonio)butyl;
3-(dodecyldimethylammonio)propyl;
3-(octyldimethylammonio)propyl;
3-(decyldimethylammonio)propyl;
5-(dodecyldimethylammonio)pentyl;
3-(cyclohexyldimethylammonio)propyl;
3-(decyldimethylammonio)-2-hydroxypropyl;
3-(tridecylammonio)propyl;
3-(docosyldimethylammonio)propyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonio)hexyl;
4-(heptyldimethylammonio)butyl;
3-(dimethylundecylammonio)propyl; and
3-(tetradecyldimethylammonio)propyl.

The polymer can be linear or cross-linked. For example, the polymer can be cross-linked by incorporation in the polymer of a multifunctional co-monomer, for example, a co-monomer comprising two or more epoxy groups. Suitable multifunctionl co-monomers include butanedioldiglycidyl ether, ethanedioldiglycidyl ether, diglycidyl 1,2-cyclohexanedicarboxylate, N,N-diglycidyl-4-glycidyloxyaniline, 1,2,7,8-diepoxyoctane, and 1,2,3,4-diepoxybutane.

The polymer can also be crosslinked by a bridging unit which links amino groups on adjacent polymer strands. For example, the polymer can comprise a repeat unit of Formula I wherein $R_1$, $R_2$ or $R_3$ is a bridging unit which connects the nitrogen atom of Formula I with a nitrogen atom on a different polymer strand. Suitable bridging units include straight chain or branched, substituted or unsubstituted alkylene groups, alkylene bis(cycloalkyl) groups, bis(alkyl) amine and tris(alkyl)amine groups, diacylalkylene groups, diacylarene groups and alkylene bis(carbamoyl) groups. Suitable bridging units include, for example, —$(CH_2)_n$—, wherein n is an integer from about 2 to about 20; —$CH_2$—$CH(OH)$—$CH_2$—; —$C(O)CH_2CH_2C(O)$—; —$CH_2$—$CH(OH)$—$O$—$(CH_2)_m$—$O$—$CH(OH)$—$CH_2$—, —$(C_6H_{10})$—$(CH_2)_m$—$(C_6H_{10})$— and $N[(CH_2)_m]_3$—, where m is an integer from about 1 to about 4; —$C(O)$—$(C_6H_2(COOH)_2)$—$C(O)$— and —$C(O)NH(CH_2)_pNHC(O)$—, where p is an integer from about 2 to about 20; and —$(OCH_2CH_2)_x$—, where x is an integer from 1 to about 100. In another embodiment, the polymer can comprise a repeat unit of Formula I wherein $R_1$, $R_2$ or $R_3$ is a covalent bond which connects the nitrogen atom of Formula I with a nitrogen atom on a different polymer strand.

Polymers of use in the present method can be prepared using techniques known in the art of polymer synthesis. In a preferred embodiment, the polymer backbone is formed by polymerization of epichlorohydrin. The resulting poly (epichlorohydrin) is characterized by repeat units of Formula II where m is 1, n is 0 and Y is a chloromethyl group. This repeat unit can be then be functionalized, for example, by reaction with ammonia or a primary, secondary or tertiary amine, to form a repeat of Formula I.

A crosslinked polymer can be prepared by co-polymerizing epichlorohydrin and a multifunctional co-monomer. Suitable multifunctional monomers include compounds having 2 or more epoxy groups. Examples of such multifunctional monomers include butanedioldiglycidyl ether, ethanedioldiglycidyl ether, diglycidyl 1,2-cyclohexane-dicarboxylate, N,N-diglycidyl-4-glycidyloxyaniline, 1,2,7,8-diepoxyoctane, and 1,2,3,4-diepoxybutane.

A crosslinked polymer which is characterized by a repeat unit of Formula I in which $R_1$ is absent can be crosslinked by reacting the polymer with one or more crosslinking agents having two or more functional groups, such as electrophilic groups, which react with amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl chloride, epoxide, and alkyl-X, wherein X is a suitable leaving group, such as a halo, tosyl or mesyl group. Examples of such compounds include epichlorohydrin, succinyl dichloride, butanedioldiglycidyl ether, ethanedioldiglycidyl ether, pyromellitic dianhydride and dihaloalkanes. The crosslinking agent can also be an $\alpha,\omega$-alkylene diisocyanate, for example $OCN(CH_2)_pNCO$, wherein p is an integer from about 2 to about 20. The polymer can be reacted with an amount of crosslinking agent equal to from about 0.5 to 20 mole percent relative to the amino groups within the polymer, depending upon the extent of crosslinking desired.

In another embodiment, crosslinked polymers comprising a repeat unit of Formula I wherein one of $R_1$, $R_2$ and $R_3$ is a bridging group can be prepared by reacting a polymer comprising a repeat unit of Formula II wherein Y is a chloromethyl group with a crosslinking agent which comprises a bridging group which is bonded to two or more terminal amino groups (e.g., $\alpha,\omega$-diaminoalkanes). For example, a polymer comprising a repeat unit of Formula II wherein Y is a chloromethyl group can be reacted with 1,12-diaminododecane to produce a crosslinked polymer comprising a repeat unit of Formula I, wherein one of $R_1$, $R_2$ and $R_3$ is a dodecyl bridging group which links two repeat units of Formula I on adjacent polymer strands. Suitable multifunctional crosslinking agents of this type can be linear, branched, cyclic, substituted, unsubstitued, saturated or contain one or more units of unsaturation and include, 1,4-diaminobutane, 1,6-diaminohexane, 1,10-diaminodecane, 1,12-diaminododecane, N,N'-dimethyl-1,6-hexanediamine, N,N'-dibutyl-1,6-hexanediamine, N,N'-bis(3-aminopropyl)ethylenediamine, 4,4'-methylene bis(cyclohexylamine), hydrazine, tris(2-aminoethyl)amine and the like. The polymer of this embodiment can be crosslinked to the desired degree by altering the quantity of crosslinking agent that is reacted with the polymer comprising a repeat unit of Formula II.

In another aspect, the invention provides novel polymers having a polyether backbone and at least one amino or ammonium group pendant therefrom as described herein.

The present invention further relates to polymers having a polyether backbone and at least one amino or ammonium group pendant therefrom, as described herein, for use in therapy (including prophylaxis) or diagnosis, and to the use of such a polymer for the manufacture of a medicament for the treatment of a particular disease or condition as described herein (e.g., atherosclerosis, hypercholesterolemia).

Polymers of use in the present method are, preferably, of a molecular weight which enables them to reach and remain in the gastrointestinal tract for a sufficient period of time to sequester a significant amount of bile acid. The polymers are, thus, of sufficient size or are sufficiently crosslinked so as to minimize or prevent their absorption from the mammalian gastrointestinal tract. Suitable linear or branched (non-crosslinked) polymers of the invention are of a molecular weight greater than about 2,000 Daltons. Crosslinked polymers, however are not generally characterized by molecular weight. The crosslinked polymers discussed herein are, preferably, sufficiently crosslinked to resist absorption from the mammalian gastrointestinal tract.

The polymers of the invention are non-toxic and stable when ingested by a mammal. By "non-toxic" it is meant that when ingested in therapeutically effective amounts neither the polymers themselves nor any ions released into the body upon ion exchange are harmful. By "stable" it is meant that when ingested in therapeutically effective amounts the polymers do not decompose, in vivo, to form potentially harmful by-products, and remain substantially intact so that they can transport material out of the body.

The polymer can be administered orally to a patient in a dosage of about 1 mg/kg/day to about 1 g/kg/day, preferably between about 1 mg/kg/day to about 200 mg/kg/day. The particular dosage can depend on the individual patient (e.g., the patient's weight, age and the extent of bile acid sequestration required). The polymer can be administered either in hydrated or dehydrated form, and can be flavored or added to a food or drink, if desired, to enhance patient acceptance. Additional inert ingredients, such as artificial coloring agents, may be added as well.

Examples of suitable forms for administration include pills, tablets, capsules, and powders (i.e. for sprinkling on food). The pill, tablet, capsule or powder can be coated with a substance capable of protecting the composition from the gastric acid in the patient's stomach for a period of time sufficient for the composition to pass undisintegrated into the patient's small intestine. The polymer can be administered alone, admixed with a carrier, diluted by a carrier, or enclosed within a carrier which may be in the form of a capsule, sachet, paper or other container. When the carrier serves as a diluent, it may be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carriers, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates and talc.

The methods described herein can comprise the administration of a polyether-based polymer of the invention in combination with any known or later developed antihyperlipoproteinemic or cholesterol lowering agent or agents, for example, aryloxyalkanoic acid derivatives, HMG CoA reductase inhibitors, nicotinic acid derivatives, thyroid hormones and analogs and other bile acid sequestrants to bind bile acids, reduce blood cholesterol, treat atherosclerosis and/or treat hypercholesterolemia.

The invention will now be further and specifically described by the following examples. All parts and percentages are by weight unless otherwise specified.

EXAMPLES

Example 1

Functionalization of Poly(epichlorohydrin) with Dimethylamine

To a 1 L 3-necked, round-bottomed flask equipped with a jacketed condenser with circulating water/ethylene glycol mixture chilled to −10° C., a mechanical stirrer, a heating mantle and a thermowatch were added 20.0 g poly (epichlorohydrin) (high molecular weight), 200 mL 40% dimethylamine in water and 200 mL water. The reaction mixture was stirred and heated to 70° C. for 24 hours. After 24 hours, the solid was white, slightly more broken up and jelly-like. The reaction mixture was removed from the heat, and transferred to a blender. To the blender was also added 100 mL 40% dimethylamine in water. The mixture was blended at high speed for one minute, breaking up the solid and forming a white, smooth and thick mixture. This mixture was returned to the reaction flask. The blender was rinsed with 100 ml of the 40% dimethylamine which was then also added to the reaction flask. The mixture was then heated to 70° C. The mixture remained white and became extremely thick. The flask was wrapped in glass wool and heating was continued without stirring for 96 hours. A 200 mL portion of 40% dimethylamine was then added and the mixture was stirred with a mechanical stirrer. The temperature was then increased to 100° C. for 2.5 hours. The flask was then removed from the heat and cooled to room temperature. The mixture was then evaporated using a rotary evaporator for one hour in a 70° C. water bath, resulting in a decrease in mass of 369.3 grams. The flask was placed under vacuum overnight at room temperature. The solid residue was then transferred to a drying tray. Wet weight of the residue was 258.5 grams. The solid was then dried overnight in a forced air oven at 60° C., after which time the mass of the solid was 31.4 grams.

Elemental Analysis (% by weight): carbon: 39.57; hydrogen: 8.25; nitrogen: 9.26; chlorine: 21.41.

Example 2

Functionalization of Poly(epichlorohydrin) with Dimethylamine

To a 500 mL, 3-necked, round-bottomed flask equipped with a jacketed condenser with circulating water/ethylene glycol mixture chilled to −20° C., a mechanical stirrer, a heating mantle and a thermowatch were added 10.0 g poly(epichlorohydrin) (high molecular weight), 100 mL 40% dimethylamine in water and 100 mL water. The resulting mixture was heated to 65° C. with stirring for 22 hours. The resulting solid was off-white. The reaction flask was removed from the heat, and the reaction mixture was transferred to a blender and blended at high speed for one minute. This caused the solid to break up and form an off-white mixture. The blended mixture was returned to the reaction flask. The blender was rinsed with 100 ml of 40% dimethylamine in water and 100 mL water and the rinses were also added to the reaction flask. The mixture was then heated to 70° C. for 6 hours and then removed from the heat. The mixture was then transferred to a 1 L beaker. The volume of the mixture was increased to 800 mL by adding 50/50 (v/v) 40% dimethylamine/water. Using a slotted screen, the mixture was sheared for 30 seconds with a mixer. The mixture was then transferred to a 1 L, 3-necked, round-bottomed reaction flask and heated to 70° C. for 72 hours. The temperature was then increased to 80° C. for 24 hours. The mixture was then cooled with an ice bath to 20° C., poured into a 5 L beaker, and diluted to 5 L with isopropanol. The resulting mixture was stirred 2 hours and then filtered. Wet weight=10.6 grams. Two grams of the wet solid were removed for analytical testing and the remainder was dried overnight in a 60° C. forced air oven. Dry yield=3.4 g.

Elemental Analysis (% by weight): carbon: 48.93; hydrogen: 9.66; nitrogen: 8.81; chlorine: 12.93.

Example 3

Crosslinking of Polyepichlorohydrin with Diaminododecane Followed by Alkylation with Trimethylamine To a 2 L, 3-necked, round-bottomed flask equipped with a jacketed condenser with circulating water/ethylene glycol mixture chilled to −10° C., a mechanical stirrer, a heating mantle, and a thermowatch were added 20.0 grams of poly(epichlorohydrin) and 240 mL dimethylformamide. The resulting mixture was stirred to dissolve the polymer. The solution was heated to 70° C. and 21.7 g (0.108 mol) 1,12-diaminododecane was added. The solution gelled after two hours. The flask was wrapped in towels and heating was continued for 4 hrs. The gel was stirred with a mechanical stirrer and removed from the heat. The reaction mixture then stood for 64 hours at room temperature. After adding 470 mL dimethylformamide, the mixture was stirred for 3 hours, resulting in a swollen gel. 50 mL isopropanol was then added and the mixture was cooled in an ice bath. Trimethylamine (160.2 g) was then bubbled directly into the reaction mixture, which was then stirred overnight at room temperature. The temperature was gradually increased to 70° C. over the course of 8 hours and maintained at this temperature overnight. The temperature was then increased to 80° C. for four hours, and then to 90° C. overnight. The temperature was then increased to 95° C. and maintained overnight. The mixture was then cooled to room temperature and transferred to an 8 L bucket. Water (4 L) was then added and the mixture was stirred for two hours. The mixture was acidified with 35.6 g concentration hydrochloric acid (pH=1.74). After settling for several hours, the supernatant was decanted into a clean beaker. The solid residue was transferred to a drying tray and placed in 60° C. forced air overnight. Dry yield=10.4 grams. After settling for 72 hours, the supernatant was decanted and the remaining solid residue was transferred to a drying tray and dried overnight in a 60° C. forced air oven. Dry yield=9.3 grams. Total dry yield=19.7 grams.

Example 4

Functionalization of Poly(epichlorohydrin) with Ammonia, Followed by Crosslinking with Epichlorohydrin To a 1 L, 3-necked, round-bottomed flask equipped with a jacketed condenser with circulating water/ethylene glycol mixture chilled to −10° C., a mechanical stirrer, a heating mantle and a thermowatch was add 400 mL dimethylformamide. After the flask was cooled in an ice bath, 10 g $NH_3$ gas was added, followed by 10.0 g poly(epichlorohydrin). The mixture was then stirred overnight at room temperature to dissolve the polymer. The solution was then heated to 90° C. for 24 hours to form a cloudy pink mixture, which was then cooled in an ice bath to less than 30° C. At this point, the pH of the reaction mixture was 10.4. The mixture was evaporated with a rotary evaporator in a 90° C. water bath, yielding 25.64 g of a thick brick-red sludge. The sludge was stirred in a mixture of 40 ml $H_2O$ and 50 ml methanol and then heated in a 70° C. water bath for one hour. The pH at this point was 4.5. Sufficient 50% aqueous sodium hydroxide was then added to raise the pH to 6.3. The solvent was decanted, and 40 mL dimethylformamide was added to the remaining sludge. The mixture was heated to dissolve the solids and then cooled to room temperature, yielding a deep rose-colored solution of pH 10.2. Epichlorohydrin (0.497 g; 0.00537 mol) was then added and the solution was covered with plastic wrap and stirred at room temperature for three days. An additional 0.497 g (0.00537 mol) epichlorohydrin was then added and the solution was heated gently in a water bath. After several hours, the mixture gelled. The gel was then blended in 4 cups $H_2O$, filtered and washed several times with water. Wet weight=220.6 grams. The gel was then dried in a 60° C. forced air oven to afford 4.8 g dried polymer.

Example 5

Alkylation of Functionalized Polyepichlorohydrin with 1-Bromodecane

To a 1 L, 3-necked, round-bottomed flask equipped with an air condenser, a mechanical stirrer, a heating mantle and a thermowatch were added 10.0 g polyepichlorohydrin (functionalized with dimethylamine; 0.010 mol based on monomer weight of 100.14 grams/mol), 44.2 g 98% 1-bromodecane (0.20 mol) and 150 ml isopropanol/50 ml $H_2O$. The resulting mixture was heated to 70° C. The pH was adjusted to 12 by adding 6.3 g 50% aqueous sodium hydroxide. Concentrated hydrochloric acid (1.2 g) was then added to adjust pH to 10.8. After 1 hr the pH decreased to 8.25. The pH was adjusted to 10.6 by adding 1.1 g 50% aqueous sodium hydroxide, and heating was continued at 70° C. After 3 more hours, the pH was 8.20 and was adjusted to 11.5 by adding 0.7 gram 50% aqueous sodium hydroxide. Concentrated hydrochloric acid (0.5 g) was then added to lower the pH to 10.07. After 1.5 more hours, the pH was 9.05, and 0.2 g 50% aqueous sodium hydroxide was added to increase the pH to 11.6. Concentrated hydrochloric acid (2 drops) was then added to adjust the pH to 10.9. The reaction mixture was heated for an additional 24 hours. The mixture was then filtered and the solid material was washed sequentially with 750 mL methanol (three times) and 750 mL 2M sodium chloride (three times). The solid was then washed with 4.0 L water and then slurried in 1.0 L $H_2O$. The stirring slurry had a conductivity of 0.37 mS/cm and a pH of 5.13. Concentrated hydrochloric acid (3.0 mL) was then added to the stirring slurry, resulting after 20 minutes in a pH of 1.93. The slurry was filtered. The filter cake wet weight was 51.8 g. The solid was placed in a 60° C. forced air oven overnight to yield 8.4 g of dried polymer.

Example 6

Alkylation of Crosslinked, Functionalized Polyepichlorohydrin with (4-Chlorobutyl) dimethyldodecylammonium Bromide To a 500 mL, 3-necked, round-bottomed flask equipped with an air condenser, a mechanical stirrer, a heating mantle and a thermowatch were added 4.2 g polyepichlorohydrin (functionalized with ammonia and crosslinked with epichlorohydrin), 34.9 g of 70% (in methanol) (4-chlorobutyl)dodecyldimethylammonium bromide (0.063 mol) and 62.7 mL $H_2O$. The pH of the mixture was adjusted to about 10 by adding 50% aqueous sodium hydroxide. The resulting mixture was heated to 70° C. After 0.5 hrs, pH had dropped to 7.4. The pH was adjusted to about 10 with 50% aqueous sodium hydroxide. Heating at 70° C. was then continued for a total of 22 hours, after which the pH was about 0.2. The reaction mixture was then transferred to a blender and blended on low for one minute. The reaction mixture was then returned to the flask and 34.9 g 70% (in methanol) (4-chlorobutyl)dimethyldodecylammonium bromide (0.063 mol) was added.

The pH was adjusted to 9.9 with 50% aqueous sodium hydroxide. After 2 hours, the pH was about 1.5 and was adjusted to about 11.1 with 50% aqueous sodium hydroxide. Heating at 70° C. was continued for 16 hours, then the mixture was cooled in an ice bath to less than 30° C. and filtered to yield a brown, gummy solid. Wet weight: 6.4 grams. The solid was washed sequentially with 0.5 L methanol (three times) then 0.35 L 2M sodium chloride (three times) then once with $H_2O$, filtering between washes. Stirring conductivity of the $H_2O$ wash was 0.45 mS/cm at pH 5.0. Concentrated hydrochloric acid (2.0 mL) was then added to adjust the pH to 2.5. The mixture was then filtered to provide a solid (wet weight: 8.4 grams), which was dried in a 60° C. forced air oven overnight.

Dry yield=3.2 grams.

Example 7

Synthesis of Amine Modified Polyepichlorohydrin Bile Acid Sequestrants

A mixture of polyepichlorohydrin (10.0 g) and dimethylformamide (120 mL) was heated at 90° C. for 4 h until all of the polyepichlorohydrin dissolved. Then 1,12-diaminododecane (21.6 g) was added and the mixture was heated at 70° C. for 32 h, 30 min. A gel formed after the first 3 h of heating. After cooling to room temperature, the polymer gel was blended with methanol (1.5 L), and the mixture was allowed to settle. The top layer was decanted from the bottom layer, and the bottom layer was filtered. The filtered polymer was suspended in deionized water (1/2 L) and concentrated HCl was added to the suspension until the pH was 1.4. After stirring for 10 min, the suspension was filtered, and the wet polymer was dried in a forced-air oven at 60° C. to afford 11.6 g of a solid.

Examples 8–56 were prepare by modifying the reaction conditions of Example 7 and using the appropriate reagents, as indicated in Table I.

TABLE I

| | | Polyepichlorohydrin/Amine Polymers | | |
| --- | --- | --- | --- | --- |
| Example | Reagents (amount) | Solvent (amount) | Temperature | Time |
| 8 | Polyepichlorohydrin (10.0 g) dimethylamine (300 mL 40% aqueous solution added in 3 portions) | $H_2O$ (300 mL) | 100° C. | 2.5 d |
| 9 | Polyepichlorohydrin (10.0 g) dimethylamine (100 mL of 40% | $H_2O$ (100 mL | 100° C. | 5 d |

TABLE I-continued

Polyepichlorohydrin/Amine Polymers

| Example | Reagents (amount) | Solvent (amount) | Temperature | Time |
|---|---|---|---|---|
| | aqueous solution initially then 100 mL added after 3 d) | initially then 100 mL after 3 d) | | |
| 10 | Polyepichlorohydrin (10.0 g) trimethylamine (78.4 g of condensed gas) | DMF (400 mL) | 25° C. slowly to 70° C. | 4 d |
| 11 | Polyepichlorohydrin (10.0 g) dimethyldodecylamine (20.7 g) diaminododecane (1.1 g) | DMF (120 mL) | 70°–90° C. | 72 h |
| 12 | Polyepichlorohydrin (10.0 g) butylamine (35 mL) | DMF (120 mL) | 90° C. | 24 h |
| 13 | Polyepichlorohydrin (10.0 g) diaminododecane (1.1 g) butylamine (35 ml) | DMF (120 mL) | 70° C. | 94 h |
| 14 | Polyepichlorohydrin (10.0 g) diaminododecane (1.1 g) dimethyldodecylamine (24.2 g) | DMF (120 mL) | 70° C. | 15.5 h |
| 15 | Polyepichlorohydrin (19.7 g) diaminododecane (2.2 g) dimethyldodecylamine (47.7 g) | DMF (240 mL) | 70° C. | 5 days |
| 16 | Polyepichlorohydrin (20.0 g) diaminododecane (2.2 g) dimethylbutylamine (34 mL) | DMF (240 mL) | 70° C. | 4 days |
| 17 | Polyepichlorohydrin (10.0 g) diaminododecane (1.1 g) dimethyldodecylamine (24.2 g) | toluene (120 mL) | 90° C. | 20 h |
| 18 | Polyepichlorohydrin (10.0 g) dimethyldodecylamine (34.6 g) | toluene (120 mL) | 90° C. | 7 days |
| 19 | Polymer of Example 50 (5.0 g) concentrated HCl (to pH = 0.9) | H$_2$O (500 mL) | 25° C. | 1 h |
| 20 | Polymer of Example 20 evaporated | | | |
| 21 | Polymer of Example 1 (5.0 g) conc HCl (to pH =) | H$_2$O (500 mL) | 25° C. | 1 h |
| 22 | Polymer of Example 10 (5.0 g) concentrated HCl (to pH = 1) | H$_2$O (500 mL) | 25° C. | 1 h |
| 23 | Polyepichlorohydrin (10.0 g) diaminododecane (21.6 g) | DMF (120 mL) | 70° C. | 32 h |
| 24 | Polyepichlorohydrin (10.0 g) dimethylbutylamine (21.9 g) | DMF (120 mL) | 70° C. | 24 h |
| 25 | Polyepichlorohydrin (10.0 g) dodecylamine (20.0 g) | DMF (125 mL) | 70° C. | 4 days |
| 26 | Polyepichlorohydrin (10.0 g) NaOH (120 mL of a 50% soln in water) | H$_2$O (120 mL) | 90° C. | 5 days |
| 27 | Polyepichlorohydrin (10.0 g) diaminobutane (5.43 mL) | DMF (120 mL) | 70° C. | 24 h |
| 28 | Polyepichlorohydrin (10.0 g) 1,12-diaminododecane (5.4 g) then 3-dimethylaminopropylamine (30 mL) | DMF (120 mL) then (120 mL) | 70° C. | 42 h |
| 29 | Polyepichlorohydrin (20.0 g) 3-dimethylaminopropylamine (30 mL) | DMF (120 mL) | 70° C. | 21 h |
| 30 | Polyepichlorohydrin (20.0 g) 1,12-diaminododecane (11.0 g) then dodecylamine (83.8 g) | DMF (120 mL) then (120 mL) | 70° C. | 31 h |
| 31 | Polyepichlorohydrin (20.0 g) 1,12-diaminododecane (11.0 g) then N-methyloctadecylamine (25.2 g) | DMF (120 mL) then (120 mL) | 70° C. | 75 h |
| 32 | Polymer of Example 36 (10.0 g) bromodecane (28.5 g) NaOH (9 g of 50% NaOH in H$_2$O added in portions) | IPA (150 mL) H$_2$O (50 mL) | 70° C. | 21 h |
| 33 | Polyepichlorohydrin (11.1 g) 1,12-diaminododecane (5.8 g) | DMF (120 mL) | 70° C. | 27 h |
| 34 | Polyepichlorohydrin (10.0 g) 3-dimethylaminopropylamine (13.84 mL) | DMF (120 mL) | 70° C. | 22.5 h |

TABLE I-continued

Polyepichlorohydrin/Amine Polymers

| Example | Reagents (amount) | Solvent (amount) | Temperature | Time |
|---|---|---|---|---|
| 35 | Polyepichlorohydrin (11.1 g) 1,12-diaminododecane (5.8 g) | toluene (70 mL) | 100° C. | 26 h |
| 36 | Polyepichlorohydrin (10.0 g) N,N'-dimethyl-1,6-hexanediamine (4.83 mL) | DMF (60 mL) | 70° C. | 20 h |
| 37 | Polyepichlorohydrin (10.0 g) N,N'-dimethyl-1,6-hexanediamine (4.83 mL) | toluene (60 mL) | 100° C. | 20 h |
| 38 | Polymer of Example 31 (5.0 g) $K_2HCO_3$ (27.0 g) methyliodide (35 mL) | MeOH (100 mL) | 25° C. | 3 days |
| 39 | Polyepichlorhydrin (10.0 g) N,N'-dimethyl-1,6-hexanediamine (19.67 mL) | DMA (60 mL) | 70° C. | 19 h |
| 40 | Polymer of Example 42 (5.0 g) NaOH (added 50% NaOH until pH 10, adjusted with conc HCl) epichlorohydrin (0.204 mL) | $H_2O$ (20.0 g) | 25° C. | 21 h |
| 41 | Polymer of Example 48 (3.0 g) bromodecane (16 mL) NaOH (4 drops of 50% NaOH in $H_2O$ added in portions) | IPA (25 mL) $H_2O$ (25 mL) | 75° C. | 18 h |
| 42 | Polyepichlorohydrin (10.0 g) dimethylamine (100 mL of 40% aqueous solution) | DMF (120 mL) | 60° C. | 24 h |
| 43 | Polyepichlorohydrin (10.0 g) 1,12-diaminododecane (1.1 g) | DMF (120 mL) | 70° C. | 20.5 h |
| 44 | Polyepichlorohydrin (10.0 g) dimethylamine (120 mL of 2M THF solution) | DMF (120 mL) | 60° C. | 40 h |
| 45 | Polymer of Example 9 (5.0 g) bromodecane (11.2 g) NaOH (add dropwise until pH 10) | $H_2O$ (51 mL) | 75° C. | 18 h |
| 46 | Polymer of Example 51 (5.0 g) dimethyldodecylamine (57.6 g) | DMF (120 mL) | 100° C. | 48 h |
| 47 | Polyepichlorohydrin (10.0 g) $NH_3$ (815 mL of 0.5M dioxane solution in two portions) | | 80° C. | 10 d |
| 48 | Polymer of Example 9 (4.0 g) bromodecane (47.8 g) | DMF (100 mL) | 70°–100° C. | 48 h |
| 49 | Polyepichlorohydrin (10.0 g) dimethyldodecylamine (34.6 g) | DMF (120 mL) | 70°–90° C. | 22 h |
| 50 | Polyepichlorohydrin (10.0 g) 4,4'-methylenebis(cyclohexylamine) (26.2 g) | DMA (50 mL) | 70° C. | 12 h |
| 51 | Polyepichlorohydrin (10.0 g) N,N'-dibutyl-1,6-hexanediamine (20.5 g) | DMA (50 mL) | 70° C. | 12 h |
| 52 | Polyepichlorohydrin (10.0 g) tris(2-aminoethyl)amine (16.47 mL) | DMA (50 mL) | 70° C. | 12 h |
| 53 | Polyepichlorohydrin (100.0 g) N,N'-bis(3-aminopropyl)ethylenediamine (20.14 mL) | DMA (50 mL) | 70° C. | 12 h |
| 54 | Polyepichlorohydrin (10.0 g) hydrazine (3.43 mL) | THF (50 mL) | 60° C. | 12 h |
| 55 | Polyepichlorohydrin (5.0 g) hydrazine (30 mL in 2 portions) | | 50–75° C. | 7 days |
| 56 | Polyepichlorohydrin (10.0 g) 1,12-diaminododecane (1.0 g) then dimethyldodecylamine (40 g) | toluene (200 mL) then di(ethylene glycol)butyl ether (250 mL) | 70°–100° C. | 4 days |

In Vivo Methods

The in vivo bile acid sequestration properties of polymers prepared according to the invention have been evaluated using hamsters as the animal model. The results suggest that the polymers of the invention are highly potent bile acid sequestrants.

Example 57

Determination of Bile Acid Excreted

After a week of acclamation to our facility, hamsters were transferred to special cages that separate urine and feces. They were given only water for a 24 hour period in order to synchronize their urge for food as a group. Following the 24 hour fast, they were presented a casein-based purified feed with 10% fat added plus a predetermined amount of the drug. The control group was given no drug. The food was presented for a 72 hour period. Fecal material was collected for 63 hours, from the 9th to the 72nd hour. We were able to detect the point at which the animals began excreting the drug-containing diet due to the contrast in color (dark brown to white) in the two feeds. The fecal material was then freeze-dried to eliminate water weight from the material. It was then pulverized with an amalgamator to a uniform powder, and 1 g was placed in the extraction cell. A solution of 80% methanol in 100 mMol NaOH was used as the extraction solvent since it is a solvent most bile acids are sufficiently soluble in and is basic enough to hydrolyze bile acid esters. The esters commonly occur in the feces and become difficult to extract if not hydrolyzed. The extraction was accelerated by holding the sample and solvent at 100° C. and 1500 psi. 0.25 mL of the extract was evaporated and reconstituted in bovine calf serum. The sample was then analyzed like a standard serum sample, enzymatically, for bile acid concentration. The concentration was multiplied by four times the volume of extract and expressed as the concentration per gram of feces. The results are presented in Table II.

TABLE II

In Vivo Bile Acid Extraction.

| Example # | Dose | Bile Acid Mass Excreted ($\mu$mol/g) | % Above Control |
|---|---|---|---|
| 3 | 0.20% | 1.55 | 66 |
| 5 | 0.20% | 4.60 | 395 |
| 19 | 0.20% | 2.44 | 162 |
| 21 | 0.20% | 1.51 | 63 |
| 22 | 0.20% | 2.40 | 158 |
| 23 | 0.20% | 3.79 | 524 |
| 30 | 0.20% | 4.41 | 241 |
| 36 | 0.20% | 3.92 | 230 |
| 38 | 0.20% | 3.23 | 246 |
| 41 | 0.20% | 5.70 | 511 |
| 50 | 0.10% | 2.77 | 211 |
| 52 | 0.10% | 1.68 | 89 |
| 53 | 0.10% | 1.63 | 83 |
| CholestaGel | 0.15% | 4.33 | 265 |
| Colestipol | 0.30% | 2.31 | 110 |
| Cholestyramine | 0.30 | 3.00 | 125 |

While this invention has been particularly shown and described with references to preferred embodiments thereof, it will be understood by those skilled in the art that various changes in form and details may be made therein without departing from the scope of the invention encompassed by the appended claims.

We claim:

1. A method for sequestering bile acids in a patient comprising orally administering to the patient a therapeutically effective amount of a crosslinked polyether copolymer comprising a repeat unit of the general formula:

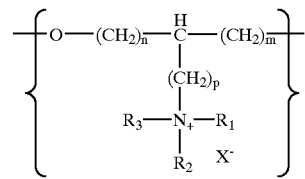

wherein n and m are each, independently, 0, 1 or 2;

p is an integer from 0 to about 6;

$R_1$, $R_2$ and $R_3$ are each, independently, a hydrogen atom; a substituted or unsubstituted, linear, branched or cyclic alkyl group; or a substituted or unsubstituted aryl group; and $X^-$ is a pharmaceutically acceptable anion; or if at least one of $R_1$, $R_2$ and $R_3$ is hydrogen, the unprotonated basic form thereof.

2. The method of claim 1 wherein $X^-$ is an anion selected from the group consisting of chloride, bromide, citrate, tartrate, lactate, methanesulfonate, acetate, formate, maleate, fumarate, malate, succinate, malonate, sulfate, L-glutamate, L-aspartate, pyruvate, mucate, benzoate, glucuronate, oxalate, ascorbate, acetylglycinate and the conjugate base of a fatty acid.

3. The method of claim 1 wherein at least one of $R_1$, $R_2$ and $R_3$ is an alkyl group substituted with one or more substituents or an aryl group substituted with one or more substituents, wherein said substituents are selected from the group consisting of fluorine, chlorine, bromine, iodine, alkyl, hydroxy, primary, secondary and tertiary amino, quaternary ammonium, alkoxy, carboxamido, sulfonamido, aryl, hydrazido, guanidyl, and ureyl.

4. The method of claim 1 wherein at least one of $R_1$, $R_2$ and $R_3$ is a hydrophobic alkyl group having from 4 to about thirty carbon atoms.

5. The method of claim 4 wherein the hydrophobic alkyl group is selected from the group consisting of n-octyl, n-nonyl, n-decyl, n-undecyl, n-dodecyl, n-tridecyl, n-tetradecyl, n-pentadecyl, n-hexadecyl, n-heptadecyl and n-octadecyl.

6. The method of claim 1 wherein n is 1, m is 0 and p is 1.

7. The method of claim 3 wherein at least one of $R_1$, $R_2$ and $R_3$ is a group of the formula:

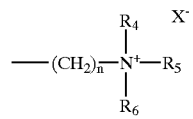

wherein $R_4$, $R_5$ and $R_6$ are each, independently, a hydrogen atom or a $C_1$–$C_{24}$ alkyl group; n is an integer from 2 to about 20; and $X^-$ is a pharmaceutically acceptable anion.

8. The method of claim 7 wherein $X^-$ is an anion selected from the group consisting of chloride, bromide, citrate, tartrate, lactate, methanesulfonate, acetate, formate, maleate, fumarate, malate, succinate, malonate, sulfate, L-glutamate, L-aspartate, pyruvate, mucate, benzoate, glucuronate, oxalate, ascorbate, acetylglycinate and a conjugate base of a fatty acid.

9. The method of claim 1 wherein the copolymer is further characterized by a repeat unit of the general formula:

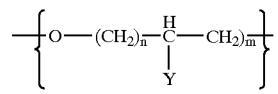

wherein n and m are each 0, 1 or 2; and Y is a hydrogen atom, an alkyl group or a chloromethyl group.

10. The method of claim 1 wherein the copolymer is crosslinked by a multifunctional co-monomer.

11. The method of claim 10 wherein the multifunctional co-monomer is characterized by two or more epoxy groups.

12. The method of claim 11 wherein the multifunctional co-monomer is selected from the group consisting of butanedioldiglycidyl ether, ethanedioldiglycidyl ether, diglycidyl 1,2-cyclohexanedicarboxylate, N,N-diglycidyl-4-glycidyloxyaniline, 1,2,7,8-diepoxyoctane and 1,2,3,4-diepoxybutane.

13. The method of claim 1 wherein the copolymer is crosslinked by a bridging unit which connects an amino or ammonium nitrogen atom on a first copolymer strand to an amino or ammonium nitrogen atom on a second copolymer strand, said bridging unit being selected from the group consisting of, straight chain or branched, substituted or unsubstituted alkylene groups, alkylene bis(cycloalkyl) groups, bis(alkyl)amine groups, tris(alkyl)amine groups, diacylalkylene groups, diacylarene groups and alkylene bis (carbamoyl) groups.

14. The method of claim 13 wherein said bridging unit is selected from the group consisting of —$(CH_2)_n$—, —$CH_2$—$CH(OH)$—$CH_2$—, —$C(O)CH_2CH_2C(O)$—;, —$CH_2$—$CH(OH)$—$O$—$(CH_2)_m$—$O$—$CH(OH)$—$CH_2$—, —$(C_6H_{10})$—$(CH_2)_m$—$(C_6H_{10})$—, $N[(CH_2)_m]_3$, —$C(O)$—$(C_6H_2(COOH)_2)$—$C(O)$—, —$C(O)NH(CH_2)_p NHC(O)$— and —$(OCH_2CH_2)_x$—; wherein:

m is an integer from 1 to about 4;

n and p are each, independently, an integer from about 2 to about 20; and x is an integer from 1 to about 100.

15. The method of claim 1 wherein the copolymer is crosslinked by a covalent bond between an amino or ammonium nitrogen atom on a first copolymer strand and an amino or ammonium nitrogen atom on a second copolymer strand.

16. A method for lowering cholesterol in a patient comprising orally administering to the patient a therapeutically effective amount of a crosslinked polyether copolymer comprising a repeat unit of the general formula:

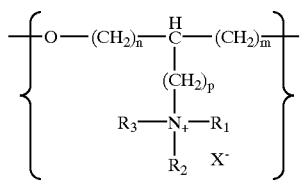

wherein n and m are each, independently, 0, 1 or 2;

p is an integer from 0 to about 6;

$R_1$, $R_2$ and $R_3$ are each, independently, a hydrogen atom; a substituted or unsubstituted, linear, branched or cyclic alkyl group; or a substituted or unsubstituted aryl group; and $X^-$ is a pharmaceutically acceptable anion; or if at least one of $R_1$, $R_2$ and $R_3$ is hydrogen, the unprotonated basic form thereof.

17. The method of claim 16 wherein $X^-$ is an anion selected from the group consisting of chloride, bromide, citrate, tartrate, lactate, methanesulfonate, acetate, formate, maleate, fumarate, malate, succinate, malonate, sulfate, L-glutamate, L-aspartate, pyruvate, mucate, benzoate, glucuronate, oxalate, ascorbate, acetylglycinate and the conjugate base of a fatty acid.

18. The method of claim 16 wherein at least one of $R_1$, $R_2$ and $R_3$ is an alkyl group substituted with one or more substituents or an aryl group substituted with one or more substituents, wherein said substituents are selected from the group consisting of fluorine, chlorine, bromine, iodine, alkyl, hydroxy, primary, secondary and tertiary amino, quaternary ammonium, alkoxy, carboxamido, sulfonamido, aryl, hydrazido, guanidyl, and ureyl.

19. The method of claim 16 wherein at least one of $R_1$, $R_2$ and $R_3$ is a hydrophobic alkyl group having from 4 to about thirty carbon atoms.

20. The method of claim 19 wherein the hydrophobic alkyl group is selected from the group consisting of n-octyl, n-nonyl, n-decyl, n-undecyl, n-dodecyl, n-tridecyl, n-tetradecyl, n-pentadecyl, n-hexadecyl, n-heptadecyl and n-octadecyl.

21. The method of claim 16 wherein n is 1, m is 0 and p is 1.

22. The method of claim 18 wherein at lease one of $R_1$, $R_2$ and $R_3$ is a group of the formula:

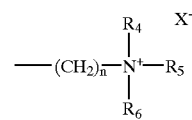

wherein $R_4$, $R_5$ and $R_6$ are each, independently, a hydrogen atom or a $C_1$–$C_{24}$ alkyl group; n is an integer from 2 to about 20; and $X^-$ is a pharmaceutically acceptable anion.

23. The method of claim 22 wherein $X^-$ is an anion selected from the group consisting of chloride, bromide, citrate, tartrate, lactate, methanesulfonate, acetate, formate, maleate, fumarate, malate, succinate, malonate, sulfate, L-glutamate, L-aspartate, pyruvate, mucate, benzoate, glucuronate, oxalate, ascorbate, acetylglycinate and a conjugate base of a fatty acid.

24. The method of claim 16 wherein the copolymer is further characterized by a repeat unit of the general formula:

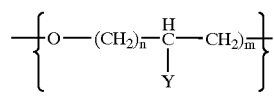

wherein n and m are each 0, 1 or 2; and Y is a hydrogen atom, an alkyl group or a chloromethyl group.

25. The method of claim 16 wherein the copolymer is crosslinked by a multi functional co-monomer.

26. The method of claim 25 wherein the multifunctional co-monomer is characterized by two or more epoxy groups.

27. The method of claim 25 wherein the multifunctional co-monomer is selected from the group consisting of butanedioldiglycidyl ether, ethanedioldiglycidyl ether, diglycidyl 1,2-cyclohexanedicarboxylate, N,N-diglycidyl-4-glycidyloxyaniline, 1,2,7,8-diepoxyoctane and 1,2,3,4-diepoxybutane.

28. The method of claim 16 wherein the copolymer is crosslinked by a bridging unit which connects an amino or ammonium nitrogen atom on a first copolymer strand to an amino or ammonium nitrogen atom on a second copolymer strand, said bridging unit being selected from the group consisting of, straight chain or branched, substituted or unsubstituted alkylene groups, alkylene bis(cycloalkyl) groups, bis(alkyl)amine groups, tris(alkyl)amine groups, diacylalkylene groups, diacylarene groups and alkylene bis (carbamoyl) groups.

29. The method of claim 28 wherein said bridging unit is selected from the group consisting of —$(CH_2)_n$—, —$CH_2$—$CH(OH)$—$CH_2$—, —$C(O)CH_2CH_2C(O)$—, —$CH_2$—$CH(OH)$—O—$(CH_2)_m$—O—$CH(OH)$—$CH_2$—, —$(C_6H_{10})$—$(CH_2)_m$—$(C_6H_{10})$—, $N[(CH_2)_m]_3$, —$C(O)$—$(C_6H_2(COOH)_2)$—$C(O)$—, —$C(O)NH(CH_2)_p NHC(O)$— and —$(OCH_2CH_2)_x$—; wherein:

m is an integer from 1 to about 4;

n and p are each, independently, an integer from about 2 to about 20; and x is an integer from 1 to about 100.

30. The method of claim 16 wherein the copolymer is crosslinked by a covalent bond between an amino or ammonium nitrogen atom on a first copolymer strand and an amino or ammonium nitrogen atom on a second copolymer strand.

* * * * *